United States Patent [19]

Carmen et al.

[11] Patent Number: 5,240,829
[45] Date of Patent: Aug. 31, 1993

[54] METHOD FOR INACTIVATING VIRUSES IN BLOOD USING CHLORINE DIOXIDE

[75] Inventors: Raleigh Carmen, Concord; Chi-Yong Chong, San Francisco, both of Calif.

[73] Assignee: Miles Inc., Elkart, Ind.

[21] Appl. No.: 309,445

[22] Filed: Feb. 10, 1989

[51] Int. Cl.⁵ .............................................. A01N 1/02
[52] U.S. Cl. .......................................... 435/2; 422/37; 435/236
[58] Field of Search ...................... 435/2, 236; 422/28, 422/29, 37; 604/410

[56] References Cited

U.S. PATENT DOCUMENTS 4,908,188  3/1990  Jefferis et al. ........................ 422/111
4,971,760  11/1990  Rubinstein ............................ 422/37

FOREIGN PATENT DOCUMENTS 8706119  10/1987  World Int. Prop. O.

Primary Examiner—David M. Naff
Assistant Examiner—S. Saucier

[57] ABSTRACT

A closed system for inactivating viruses in blood or blood components. The system includes at least one plastic bag which communicates with a separate container including a single viricidal substance or separate substances which, when mixed, provide in situ generation of a viricidal substance. The viricidal substance can be transferred into the bag for subsequent viricidal use on blood components or for use on components in the bag. A preferred system provides a means for the in-situ generation of $ClO_2$ from sterilizable, separate substances for viricidal use on blood or blood components.

5 Claims, 1 Drawing Sheet

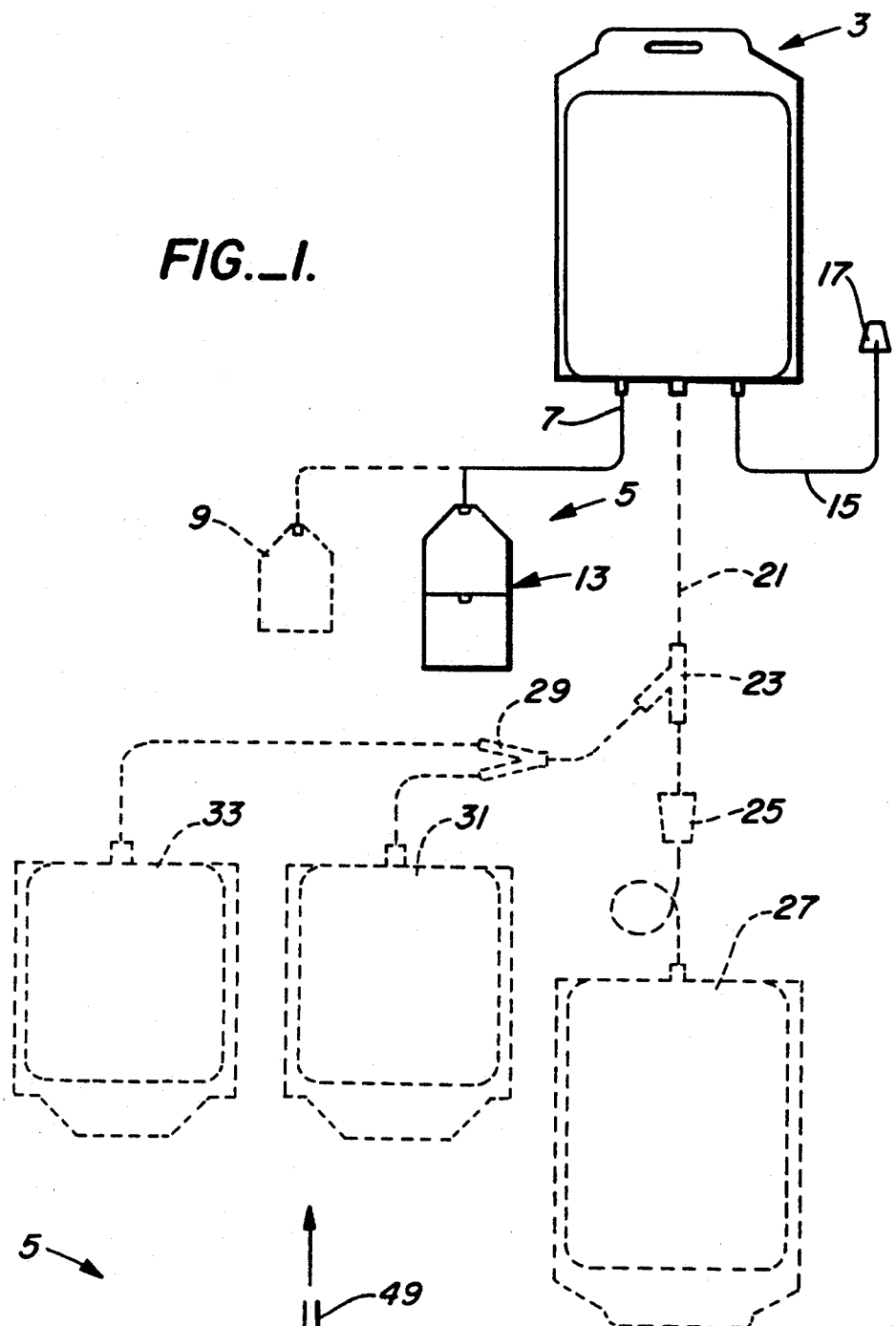
FIG._1.
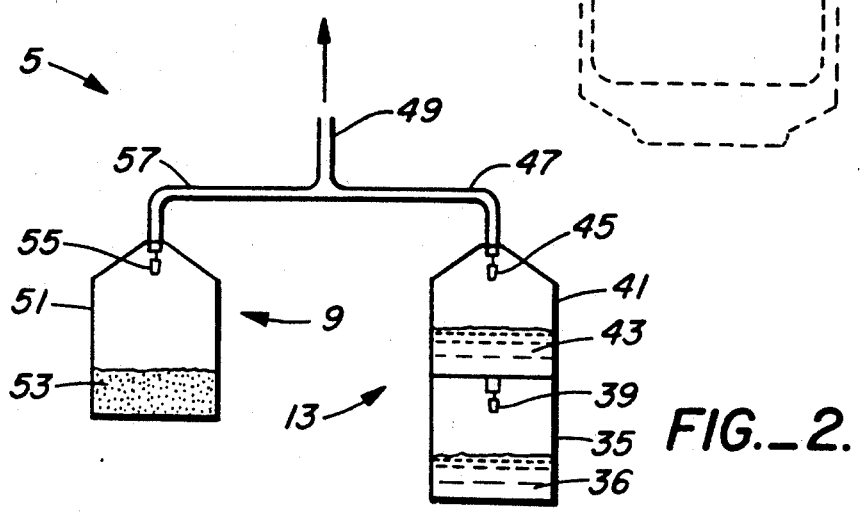
FIG._2.

METHOD FOR INACTIVATING VIRUSES IN BLOOD USING CHLORINE DIOXIDE

BACKGROUND OF THE INVENTION

1. Field

This disclosure is concerned generally with blood bag systems and specifically with a blood bag system that includes means for assuring that blood or blood components are free of infectious viruses.

2. Prior Art

Plastic bag systems for collecting, processing and storing blood or, more recently, blood components, are well known. Such systems include both single bags and multiple blood bags in sterile communication with each other via tubings and valving systems. Such single and multiple blood bag systems are known as "closed" systems since they permit the collection, processing, storing and administration of blood, blood components or other materials with minimal chance of contamination of the bag contents after blood has been collected from a donor.

The administration of blood and blood components (i.e. red blood cells, platelets and various plasma fractions such as albumin, immunoglobulins, coagulation factors and the like) may pose the risk of transmitting viruses such as hepatitis or HIV from a blood donor to a recipient of the blood or blood component. Although such risk can be minimized by testing all donor blood, it would be very desirable to have in place some back up viricidal system for all blood and blood components intended for transfusion to a recipient other than the donor.

To date, we are aware of only one system where an anti-microbial agent is intentionally included in a closed blood bag system. In U.S. Ser. No. 944,061 filed on Dec. 22, 1986, in the names of A. Champion and M. Collins, there is disclosed a blood bag system which includes a well known anti-microbial known as ciprofloxacin. In that disclosure, however, the anti-microbial agent is already present in the closed system. This can be a disadvantage when it is desirable to keep the anti-microbial separate from the bag contents until needed or if blood bag manufacturing operations call for conditions (i.e. sterilization) that might be detrimental to the anti-microbial. In addition, the disclosed system does not contemplate use of substances that may be unstable with time or substances which are effective only if generated in situ and immediately used.

Although various viricidal agents such as $ClO_2$ are well known (see U.S. Pat. No. 4,084,747 describing the use of $ClO_2$ for sanitizing and disinfecting) and the use of $ClO_2$ is known for AIDS virus inactivation (see New England J. of Med. 313:1416, 1986), we are unaware of the use or generation of such viricidal agents in a closed blood bag system. Further, although the catalytic effect of chloride on chlorine dioxide generation has been disclosed by Kieffer et al. in Inorg. Chem. 7:235 and 239, 1968, we are unaware of the use of that observation for blood bag viricidal applications.

Surprisingly, we have now found a novel system and method for assuring viricidal activity of blood components alone or, preferably, in a closed blood bag system. Details of our discovery are described below.

SUMMARY OF THE INVENTION

The viricidal bag system comprises of at least one closed plastic bag having in closed communication therewith a separate container including a viricidal substance or separated substances which, when mixed, will generate a viricidal substance which can be then transferred into the bag for subsequent viricidal action. In one embodiment, the separate container comprises two openable compartments, one containing a sodium chlorite solution and the other containing an acid solution. When the two solutions are mixed by opening a valve between the compartments, chlorine dioxide is controllably generated in situ which, by opening yet another valve, is passed into the blood bag for viricidal action. In yet another embodiment, the separate container has in communication with it a further separate container holding a buffering agent. In one use, blood or blood components are initially introduced into the blood bag (e.g. a donor bag). The separate container attached to the bag is then manipulated under conditions sufficient to generate or make available the viricidal substance which is then passed into the bag and contacted with the blood or blood component under conditions sufficient to assure inactivation of substantially all viruses present in the blood or blood component. In another use the viricidal substance is passed into a vehicle solution (such as saline solution) contained in the plastic bag and the viricidal and vehicle is then brought in contact with blood or a blood component to be treated.

BRIEF DESCRIPTION OF THE FIGURES

FIG. 1 illustrates the general system of this disclosure, showing it as part of an optional multiple blood bag system.

FIG. 2 illustrates one embodiment of separate compartments useful for the in situ generation of chlorine dioxide.

SPECIFIC EMBODIMENTS

Our viricidal plastic bag system is illustrated in FIGS. 1 and 2.

FIG. 1 shows a plastic bag 3 which may be a conventional blood bag (e.g. made from a plasticized PVC or a polyolefin) which may (preferably) or may not have connected there to conventional PVC tubing 15 terminating in a donor needle illustrated generally as item 17. In closed communication with bag 3 via conventional PVC tubing 7 is a separate container 13 which includes the means for providing or generating and providing a viricidal substance through tubing 7 into bag 3. Shown connected by dotted lines is an optional plastic bag 9 which may contain, for example, an optional buffer in powder form or in a solution. Also shown connected by dotted lines are other optional bags 27, 31 and 33 connected via conventional PVC tubing 21 using conventional Y-connectors and clamps 25. Communication between the various bags of FIG. 1 may be controlled using conventional valves, preferably so-called frangible valves that permit external manipulation and maintenance of a closed system. A very preferred valve for our system is the frangible pivoting valve disclosed in U.S. Pat. No. 4,586,928 to Barnes et al. incorporated herein by reference to it.

Bag 3 of FIG. 1 may be initially empty, contain an anticoagulant solution, or a viricide vehicle solution such as normal saline. An important feature of this invention is that bag 3 be in closed communication with a container for the viricidal substance (or ingredients for in situ generation of such substance).

FIG. 2 illustrates a more detailed and preferred viricidal subsystem 5. Subsystem 5 is connected in closed communication via conventional tubing 49 to a plastic bag (not shown in FIG. 2 but corresponding to bag 3 in FIG. 1). Tubing 49 communicates via tubing 57 to optional buffer bag 9 via frangible pivoting valve 55 to container 51 containing buffer substance 53 which may be, for example, a buffer solution or even a powder to which a diluent is added via tubing 57.

Connected via tubing 47 is a means for in situ generation of, for example, $ClO_2$ contained in subsystem container 13. Container 13 consists of two separate compartments 35 and 41 initially closed via frangible pivoting valves 45 and 39. Compartment 41 contains a sodium chlorite solution (about 10 ml, 30 millimolar) and compartment 35 contains an HCl acid solution (1-5 ml of 0.1 to 1N). Compartment 51 contains about 100 to 1000 mg $NaHCO_3$ to be used as the buffer ingredient as described below. As noted, in very preferred embodiments, chloride ions are desirably present to catalyze the $ClO_2$ production and this can be assured by including a chloride ion source with the sodium chlorite, the amount of chloride ions being sufficient to demonstrate catalysis which still maintaining, in combination with the buffer and other solutions, physiological isotonicity.

It is thought that the principles of this disclosure apply to a wide variety of viricidal agents in both liquid and solid form. To illustrate the invention, however, a substance known as chlorine dioxide and a novel method for its in situ generation is shown below.

Our work with the above viricidal system led to yet another surprising discovery of the effect of chloride on chlorine dioxide generation and how this effect can be advantageously used in our model system. Details of our preferred system and data supporting our findings are shown below.

It is well known that infectious agents (such as viruses, bacteria, and fungi) are a major concern in many fields, especially in the fields of blood and blood components preparation and storage. The use of chlorine and its compounds in water treatment for killing such pathogens has been known since the 19th century. It was not until the 1940's, however, that experimental data on its bactericidal efficiency became available. Although chlorine ($Cl_2$) and chlorine dioxide ($ClO_2$) are similar in many respects, including the fact that both are powerful oxidizing agents, $ClO_2$ has 2.5 times the oxidation capacity of $Cl_2$.

We have found that it is desirable to generate greater than 50% of $ClO_2$ from the total available $ClO_2$ in a sodium chlorite solution within about fifteen minutes for practical viricidal use of $ClO_2$ in blood and its products. This finding is illustrated in our overall invention description. We also describe an effective virus inactivating treatment for blood transfusion products by using the chloride ion as a catalyst in acid solution to increase the $ClO_2$ generating rate from a sodium chlorite solution.

It is desirable to prepare all the blood components without delay to insure adequate viability. The chlorine dioxide ($ClO_2$) generating method, described by Sarin et al. and in U.S. Pat. No. 4,084,747, is not practical to apply blood transfusion products for this purpose. The $ClO_2$ generating rate, using lactic acid and a sodium chlorite solution, is simply too slow and thus ineffective for blood banking applications.

The illustrated generation system of this invention, however, can generate about 75% of chlorine dioxide from total available $ClO_2$ in sodium chlorite solution within 10 minutes at room temperature. This is assured by using chloride ions as a catalyst (see Table 1). The method disclosed in U.S. Pat. No. 4,084,747, on the other hand, generates only 4.3% of chlorine dioxide at a reaction time of 10 minutes at room temperature (see Table 1). Although the $ClO_2$ generation of that patent can be increased by using high concentrations of lactic acid and high temperature (50° C.), those measures are detrimental to the viability of blood cells.

Blood transfusion products contain high concentrations of protein. Virus killing activity of chlorine dioxide is directly related to protein concentration. We have found that the removal of protein from erythrocyte and platelet products in a closed system prior to $ClO_2$ addition is important for effective killing of the virus (see Table 2).

The data obtained with both viruses show that a protein load of 0.5% requires a chlorine dioxide concentration of 50 ppm to effect complete viral inactivation. When the albumin level is reduced to 0.05% a chlorine dioxide concentration of 5 ppm is then capable of reducing VSV infectivity at least 5 Logs and HSV-1 at least 6 logs.

CATALYTIC EFFECT OF CHLORIDE

As noted earlier, Kieffer, et al. reported the effect of chloride ion on the formation of chlorous acid (Inorg Chem 7:239, 1968). At a hydrogen ion concentration of 1.2M, there was a change from a half-life of approximately 400 minutes in the absence of initial chloride ion to a half-life of a few minutes with 0.1M chloride added initially. The same authors also reported the overall stoichiometry of the disproportionation of chlorous acid in Inorg. Chem. 7:235, 1968. In an acidic solution (in the absence of added chloride ion which alters the reaction), the stoichiometry has been found to approximately:

$$4\ H\ ClO_2 = 2\ ClO_2 + ClO_3^- + Cl^- + 2H^+ + H_2O$$

In the presence of appreciable amount of chloride ion only small amounts of chlorate ion have been found and the stoichiometry approximates:

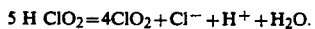

$$5\ H\ ClO_2 = 4ClO_2 + Cl^- + H^+ + H_2O.$$

As shown in Table 1, we have found that the presence of chloride in our system greatly increases the liberation of $ClO_2$ when used in our virus inactivation system. For example, 63.2% $ClO_2$ was liberated with hydrochloric acid compared to only 6.1% with sulfuric acid. Further, addition of sodium chloride increased $ClO_2$ liberation from 6.1% to 76.3%.

TABLE 1

CHLORIDE EFFECT ON CHLORINE DIOXIDE GENERATION

| (2000 ppm $ClO_2$) 30 mM $NaClO_2$ | Sodium Chloride | Acids | Reaction Time at Room Temperature | % $ClO_2$ Generated From Total Available $ClO_2$ |
|---|---|---|---|---|
| 5.0 mL | 90 mg | 1N Hcl, 5.0 mL | 10 min | 83.4 |
| 5.0 mL | 0 | 1N Hcl, 5.0 mL | 10 min | 63.2 |

TABLE 1-continued

CHLORIDE EFFECT ON CHLORINE DIOXIDE GENERATION

| (2000 ppm ClO$_2$) 30 mM NaClO$_2$ | Sodium Chloride | Acids | Reaction Time at Room Temperature | % ClO$_2$ Generated From Total Available ClO$_2$ |
|---|---|---|---|---|
| 5.0 mL | 90 mg | 1N H$_2$SO$_4$, 5.0 mL | 10 min | 76.3 |
| 5.0 mL | 0 | 1N H$_2$SO$_4$, 5.0 mL | 10 min | 6.1 |
| 5.0 mL | 90 mg | 1N Lactic Acid, 5.0 mL | 10 min | 4.3 |
| 5.0 mL | 0 | 1N Lactic Acid, 5.0 mL | 10 min | 4.3 |
| 5.0 mL | 90 mg | 1N Citric Acid, 5.0 mL | 10 min | 3.1 |
| 5.0 mL | 0 | 1N Citric Acid, 5.0 mL | 10 min | 3.1 |
| 5.0 mL | 90 mg | 1N Phosphoric Acid, 5.0 mL | 10 min | 7.4 |
| 5.0 mL | 0 | 1N Phosphoric Acid, 5.0 mL | 10 min | 4.9 |
| 5.0 mL | 90 mg | WFI, 5.0 mL | 10 min | 0.6 |

Note: Chlorine dioxide (ClO$_2$) assays were done per C. Hong, et al., Can J. Chem 46:2061, 1968

TABLE 2

PROTEIN EFFECT ON VIRUS INACTIVATION

| Albumin Conc. | Virus | Pre-Treatment Titer, Log 10 TCID50/mL | 1 hour after indicated treatment Log 10 TCID 50/mL | |
|---|---|---|---|---|
| | | | ClO$_2$, 5 ppm | ClO$_2$, 50 ppm |
| 5% | VSV | 7.5 | ≧6.5 | ≧6.5 |
| | HSV-1 | 6.5 | ≧6.5 | 6.25 |
| 0.5% | VSV | 7.75 | ≧6.5 | ≦0.5 |
| | HSV-1 | 6.75 | 5.5 | ≦0.5 |
| 0.05% | VSV | 8.0 | 1.25 | ≦0.5 |
| | HSV-1 | 7.0 | ≦0.5 | ≦0.5 |

AS-3 red blood cell (paired) storage studies show that 50 ppm of ClO$_2$ in the supernatant does not affect in vitro tests of stored red cells up to six weeks (see Table 3).

TABLE 3

AS-3 Red Blood Cell Paired Study (n = 4)

| Week | ATP (uM/gHb) | | % Hemolysis | | pH at 37° C. | | OSMOTIC FRAGILITY % (NaCl) Causing 10% Lysis | |
|---|---|---|---|---|---|---|---|---|
| | ClO$_2$ | Control | ClO$_2$ | Control | ClO$_2$ | Control | ClO$_2$ | Control |
| 0 | 6.1 ± 0.6 | 5.1 ± 0.7 | 0.05 ± 0.01 | 0.04 ± 0.02 | 6.83 ± 0.02 | 6.83 ± 0.02 | 0.68 ± 0.11 | 0.67 ± 0.07 |
| 1 | 5.6 ± 0.7 | 5.6 ± 0.9 | 0.08 ± 0.02 | 0.07 ± 0.03 | 6.69 ± 0.03 | 6.69 ± 0.02 | 0.60 ± 0.01 | 0.60 ± 0.01 |
| 2 | 5.7 ± 1.1 | 5.9 ± 1.1 | 0.13 ± 0.04 | 0.10 ± 0.06 | 6.60 ± 0.03 | 6.60 ± 0.03 | 0.59 ± 0.01 | 0.59 ± 0.01 |
| 3 | 5.4 ± 1.0 | 5.4 ± 1.0 | 0.20 ± 0.08 | 0.17 ± 0.09 | 6.54 ± 0.03 | 6.55 ± 0.03 | 0.61 ± 0.01 | 0.60 ± 0.01 |
| 4 | 4.8 ± 1.0 | 5.0 ± 1.0 | 0.32 ± 0.08 | 0.31 ± 0.16 | 6.50 ± 0.04 | 6.50 ± 0.04 | 0.62 ± 0.01 | 0.62 ± 0.01 |
| 5 | 4.0 ± 0.8 | 3.9 ± 0.7 | 0.52 ± 0.17 | 0.48 ± 0.25 | 6.46 ± 0.04 | 6.45 ± 0.04 | 0.63 ± 0.01 | 0.62 ± 0.01 |
| 6 | 3.3 ± 0.8 | 3.4 ± 0.8 | 0.97 ± 0.35 | 1.06 ± 0.55 | 6.43 ± 0.05 | 6.42 ± 0.05 | 0.61 ± 0.01 | 0.61 ± 0.01 |

ATP levels were determined by the method of enzymatic analysis. H.U. Gergmeyer, ed. 2nd printing, rev. 1965. Acad. Press. New York, pp. 559-572. In general, ATP levels tend to correlate with in vivo recovery (Dern et al., J. Lab Clin. Med., Vol. 69, 968-978, 1967).
Blood pH was determined at 37#C using a blood pH/gas analyzer (Instrumentation Laboratory system 1302).
% Hemolysis was calculated by dividing total plasma hemoglobin by total red cell hemoglobin, which was determined spectrophotometrically using Drabkin's reagent.
Osmotic Fragility was determined per Parpart et al., J. Clin. Invest., Vol 26, 636-640, 1947.

METHOD OF USE

One preferred system is used as follows:
1. Blood is collected and components prepared per AABB standard procedures. It is important to remove plasma proteins from red cell concentrate prior to adding ClO$_2$ for virus inactivation.
2. Preferably, after removal of the leukocytes by an appropriate filter system ClO$_2$ is generated and added to the packed red cell as follows:
   a) Open the device between compartment and of FIG. 1.
   b) Mix well.
   c) Incubate at room temperature for 10-15 min.
   d) Open compartment C and dissolve the dry buffering agent into the mixed solution.
   e) Immediately after neutralizing the mixed solution, add it into the packed erythrocytes.
   f) Mix well and incubate at RT for 30 minutes.
   g) Store the RBC in 4C per AABB standard procedure.

Another preferred system is used as follows:
1. Viricidal substance(s) is introduced from a separate but communicating container (e.g. 13 of FIG. 1) into a plastic bag containing a vehicle for the viricidal agent (e.g. a normal saline solution).
2. The viricidal Agent and vehicle are mixed.
3. The mixture of step 2 is mixed with a separate bag or container for blood or a blood component under conditions sufficient to assure viricidal action on the blood or blood component.

The above example of how to use is for illustrative purpose only, and is not intended for the purpose of limiting this invention. Thus, it is intended that the invention disclosed herein should be limited only the the following claims.

What is claimed is:

1. A method of inactivating viruses in blood or a blood component, the method comprising the steps of:
   a) providing a plastic bag having in controlled and closed communication therewith a container, said container including means for in situ generation of a viricidal gas substance, said generation means including a first compartment having a chloride ion source, and a second compartment having an acid solution, said first compartment being in communication with said second compartment;
b) manipulating said container under closed conditions sufficient to generate said viricidal gas substance; and
c) contacting only said viricidal gas substance with the blood or blood component under conditions sufficient to assure inactivation of substantially all viruses present in the blood or blood component.

2. The method of claim 1 wherein the viricidal substance generated in step b) is $ClO_2$ and blood or a blood component is introduced into the plastic bag prior to step b).

3. The method of claim 1 wherein the communication between the plastic bag and the container is controlled by a valving means.

4. The method of claim 3 wherein the valving means is an externally manipulable valve.

5. The method of claim 4 wherein the valve is a frangible valve.

* * * * *